US00PP29920P2

(12) United States Plant Patent
Probst

(10) Patent No.: US PP29,920 P2
(45) Date of Patent: Nov. 27, 2018

(54) ***COREOPSIS* PLANT NAMED 'SHADES OF ROSÉ'**

(50) Latin Name: ***Coreopsis* hybrid**
Varietal Denomination: Shades of Rosé

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 15/731,180

(22) Filed: Apr. 28, 2017

(51) Int. Cl.
*A01H 5/02* (2018.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen M Redden
(74) *Attorney, Agent, or Firm* — Penny J Aguirre

(57) ABSTRACT

A new cultivar of hybrid *Coreopsis* named 'Shades of Rosé' that is characterized by its sturdy, well-branched plant habit reaching an average of 50 cm in height and 90 cm in width, its floriferous and long blooming season of sterile inflorescences that do not require deadheading; bloom commences in early July and lasts until frost in Kensington, Conn., medium sized inflorescences with ray florets that are salmon-rose in color, its resistance to powdery mildew and leafspot, and its cold hardiness at least to U.S.D.A. Zone 5.

2 Drawing Sheets

Botanical classification: *Coreopsis* hybrid.
Variety denomination: 'Shades of Rosé'.

BACKGROUND OF THE INVENTION

The present invention relates to a new and distinct cultivar of *Coreopsis* plant, botanically of hybrid origin and known as *Coreopsis* 'Shades of Rosé' and will be referred to hereinafter by its cultivar name, 'Shades of Rosé'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms that do not require vernalization to intiate flowering.

The Inventor made a controlled cross in August of 2013 in New Braintree, Mass. between an unnamed and unpatented proprietary plant from his breeding program as the female parent and pollen that was pooled from a variety of unnamed and unpatented proprietary plants from his breeding program as the male parent. The exact characteristics of the pollen parent are therefore unknown. 'Shades of Rosé' was selected in September of 2014 as a single unique plant amongst the resulting seedlings.

Asexual propagation of the new cultivar was first accomplished by stem cuttings under the direction of the Inventor in Kensington, Conn. in September of 2014. Asexual propagation by stem cutting has shown that the characteristics of the new cultivar are stable and are reproduced true to type in successive generations.

SUMMARY OF THE INVENTION

The following traits have been repeatedly observed and are determined to be the characteristics of the new cultivar.

These attributes in combination distinguish 'Shades of Rosé' as a unique cultivar of *Coreopsis*.

1. 'Shades of Rosé' exhibits a sturdy, well-branched plant habit reaching an average of 50 cm in height and 90 cm in width.
2. 'Shades of Rosé' exhibits a floriferous and long blooming season of sterile inflorescences that do not require deadheading; bloom commences in early July and lasts until frost in Kensington, Conn.
3. 'Shades of Rosé' exhibits medium sized inflorescences with ray florets that are salmon-rose in color.
4. 'Shades of Rosé' exhibits resistance to powdery mildew and leafspot.
5. 'Shades of Rosé' exhibits cold hardiness at least to U.S.D.A. Zone 5.

The female parent of 'Shades of Rosé' differs from 'Shades of Rosé' in having inflorescences with ray florets that are solid pink in color. 'Shades of Rosé' can be most closely compared to *Coreopsis* cultivars 'Red Satin' (U.S. Plant Pat. No. 25,736) and 'Pink Sapphire' (U.S. Plant Pat. No. 24,288). 'Red Satin' is similar to 'Shades of Rosé' in being from a closely related breeding line to 'Shades of Rosé' in having thread-leaf type foliage and in having similar inflorescence shape and cold hardiness. 'Red Satin' differs from 'Shades of Rosé' in having inflorescences with ray florets that are red in color and slightly smaller in size and in being less vigorous. 'Pink Sapphire' is similar to 'Shades of Rosé' in having inflorescences of similar size and in having thread-like foliage. 'Pink Sapphire' differs from 'Shades of Rosé' in having inflorescences with ray florets that are purple-pink in color, in being prone to powdery mildew when grown under similar conditions in New Braintree, Mass. and in not being cold hardy in U.S.D.A. Zone 5.

BRIEF DESCRIPTION OF THE DRAWINGS

The accompanying colored photographs illustrate the overall appearance and distinct characteristics of the new

*Coreopsis*. The photographs were taken of a 5 month-old plant of 'Shades of Rosé' as grown outdoors in a one-gallon container from a 30-cell plug in Kensington, Conn.

Figure 1:
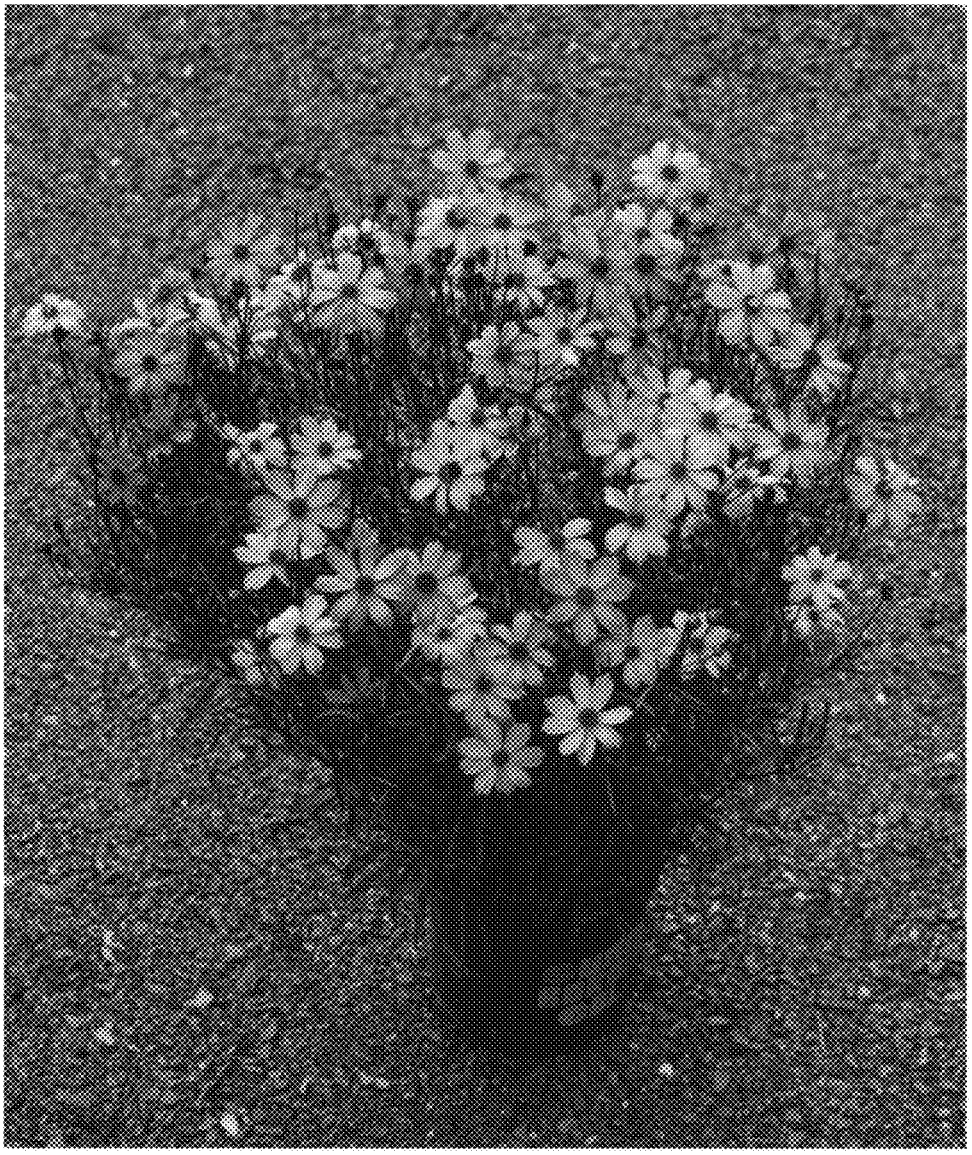

The photograph in FIG. 1 provides a side view of 'Shades of Rosé' and shows the plant habit in bloom.

Figure 2:
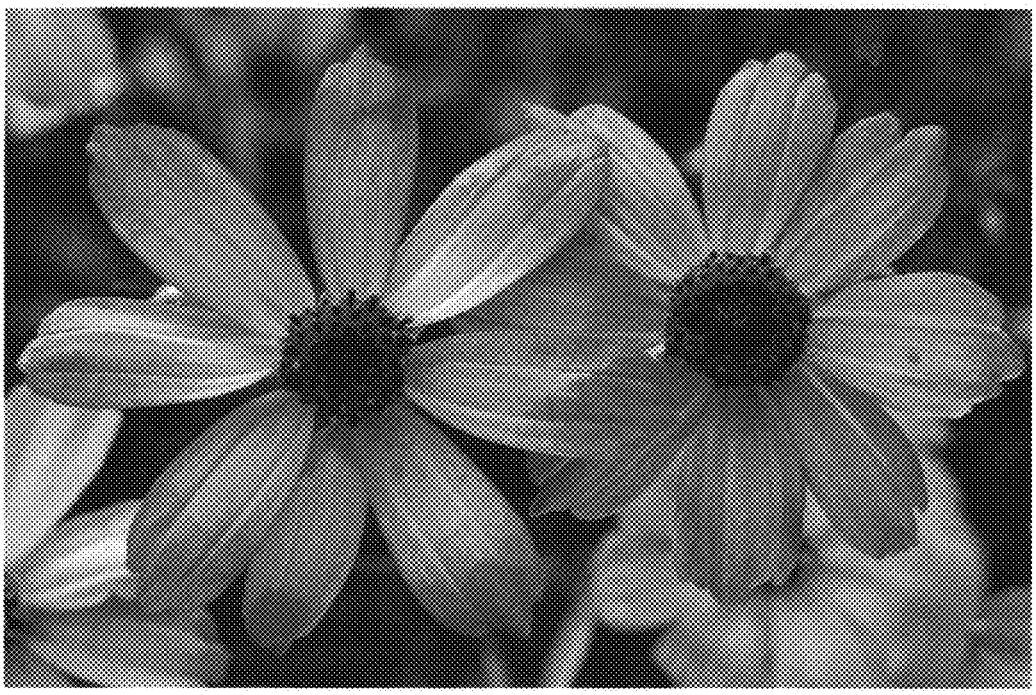

The photograph in FIG. 2 provides a close-up view of the inflorescences of 'Shades of Rosé'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 5 month-old plants of 'Shades of Rosé' as grown outdoors in a one-gallon containers from a 30-cell plugs in Kensington, Conn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms from early July until frost in Kensington, Conn.

*Plant type*.—Herbaceous perennial.

*Plant habit*.—Clump-forming, compact, upright leafy flowering stems with inflorescences held above the foliage.

*Height and spread*.—An average of 50 cm in height and 90 cm in width in the landscape.

*Cold hardiness*.—At least to U.S.D.A Zone 5a.

*Diseases and pests*.—Resistance to powdery mildew (*Podosphaera macularis*) and leafspot (*Pseudomonas cichorii*).

*Root description*.—Fibrous and fine, 161B to 161D in color.

Growth and propagation:

*Propagation*.—Stem cuttings.

*Time required for root initiation*.—An average of 10 days for root initiation.

*Growth rate*.—Vigorous.

Stem description:

*Shape*.—Rounded to tetragonal, solid.

*Stem color*.—143A.

*Stem size*.—Main stems; an average of 10 cm in length and 4 mm in width, lateral stems; an average of 14.5 cm in length (excluding peduncles) and 1.7 mm in width.

*Stem surface*.—Glabrous, smooth, and dull.

*Branching habit*.—Freely branched, an average of 10 basal main stems, lateral stems typically branched as oppositely arranaged pairs at each node, with an average of 4 lateral stems (2 pairs) per main stem.

*Internode length*.—An average of 4 cm.

Foliage description:

*Leaf division*.—Simple.

*Leaf margins*.—Entire and trifid.

*Leaf size*.—Entire leaves; an average of 7 cm in length and 4.5 mm in width, trifid leaves; center lobe an average of 6.5 cm in length and 3.5 mm in width, lateral lobes an average of 3.9 cm in length and in 2 mm width.

*Leaf shape*.—Narrow obanceolate.

*Leaf base*.—Cuneate.

*Leaf apex*.—Acute.

*Leaf venation*.—Pinnate, inconspicuous, same color as leaf.

*Leaf attachment*.—Sessile.

*Leaf arrangement*.—Opposite.

*Leaf surface*.—Upper and lower surfaces; smooth, dull, and glaucous.

*Leaf color*.—Young and mature upper surface; 137B and lower surface; 137C.

Flower description:

*Inflorescence type*.—Composite with a single row of ray florets surrounding disk florets in the center, forming a radiant head, inflorescences are borne on branch terminals in loose corymbs.

*Lastingness of inflorescence*.—8 to 10 days until senescence of ray flowers, Phyllarys and disk flowers are persistent.

*Fragrance*.—Light sweet, grassy scent.

*Quantity of inflorescences*.—Free flowering with an average of 80.

*Inflorescence size*.—Corymbs; an average of 13 cm in length and 4.5 in width, composite; an average of 1 cm in depth and 5.7 cm in diameter with disk portion up to 1.2 cm in diameter.

*Inflorescence buds*.—Globose in shape, an average of 7 mm in depth and diameter, smooth and glossy surface; color; 143A at the base fading to a blend between N144B and 22A suffused with 175A.

*Peduncle*.—Rounded in shape, strong, an average of 8.5 cm in length and 1.1 mm in diameter, 143B in color, smooth and glabrous surface.

Phyllaries (involucral bracts):

*Phyllary number*.—Two rows of 8.

*Phyllary arrangement*.—Outer phyllaries; unfused, held horizontal and recurved downwards, becoming more recurved after ray florets drop, inner phyllaries; overlap and surround receptacle with apical portion reflexed (campanulate-like).

*Phyllary size*.—Outer phyllaries; an average of 4 mm in length and 1.8 mm in width, inner phyllaries; an average of 1 cm in length and 3 mm in width.

*Phyllary color*.—Upper and lower surfaces, outer phyllaries; 143A with margins 150D, inner phyllaries; transluscent, 143B at the base, a blend of 1B, 17A, 172A and 17A at the apex.

*Phyllary texture*.—Outer phyllaries; glabrous and smooth on both surfaces, inner phyllaries; glabrous and waxy on both surfaces.

*Phyllary apex*.—Acute.

*Phyllary base*.—Truncate.

*Phyllary shape*.—Outer phyllaries; lanceolate, inner phyllaries; elliptical to lanceolate.

Ray florets (sterile):

*Number*.—8.

*Shape*.—Oblanceolate, with the appearance of 3 longitudinal sections.

*Size*.—An average of 2.8 cm in length and 1.1 cm in width.

*Apex*.—Rounded with three rounded lobes.

*Base*.—Broadly cuneate.

*Margins*.—Entire on sides with lobed apex.

*Aspect*.—Held horizontal, perpendicular to peduncle.

*Texture*.—Both surfaces; glabrous, dull, and satiny.

*Color*.—Upper and lower surfaces when opening and when fully open; a blend of 7A and 6D becoming suffused with 186C, upper surfaces when fully open; 6A at base and blending to the rest of floret with a blend of 186B to 186D, lower surfaces when fully open; 6D at base and blending to the rest of floret with a blend of 186C to 186D.

Disk florets (male and female):

*Number*.—An average of 60.

*Shape*.—Tubular, corolla is fused, flared at apex.

*Size*.—About 9 mm in length and 1 mm in width.

*Color*.—En masse; a mix between 17B and 164A, corolla; base (tube) 12A and flared portion 21A with 172A at the center.

*Receptacle*.—An average of 2.8 mm in diameter and 1 mm in depth, a blend between 138B and 191A in color.

Reproductive organs:

*Presence*.—Disk flowers only.

*Gynoecium*.—1 Pistil, an average of 6 mm in length, style is very fine and 11C to 11D in color, bifid pillose stigma is 17B in color with recurved branches about 0.7 mm in length, ovary is inferior, oblong in shape, an average of 2.1 mm in length and 1 mm in width, and 1C in color.

*Androcoecium*.—4 stamens, fused into tube surrounding style, an average of 2.5 mm in length and 0.5 mm in width, N200A in color, no pollen was observed.

*Seed*.—No seed development was observed, has been observed to be sterile.

It is claimed:

1. A new and distinct cultivar of *Coreopsis* plant named 'Shades of Rosé' as herein illustrated and described.

* * * * *